United States Patent [19]

Chastagner

[11] Patent Number: 5,319,955
[45] Date of Patent: Jun. 14, 1994

[54] TRITIUM MONITOR

[75] Inventor: Philippe Chastagner, Augusta, Ga.

[73] Assignee: United States Department of Energy, Washington, D.C.

[21] Appl. No.: 933,155

[22] Filed: Aug. 21, 1992

[51] Int. Cl.$^5$ .............. G01N 23/22; G01N 30/02
[52] U.S. Cl. .................. 73/19.02; 73/23.35; 73/23.37; 73/31.07; 976/DIG. 217; 376/256
[58] Field of Search .......... 73/19.01, 19.02, 19.1, 73/19.12, 23.35, 23.37, 23.41, 23.42, 31.07, 863.21, 863.83; 55/67, 36; 376/256; 976/DIG. 216, DIG. 217; 250/335

[56] References Cited

U.S. PATENT DOCUMENTS

| | | | |
|---|---|---|---|
| 3,411,012 | 11/1968 | Bayly | 250/43.5 |
| 3,666,942 | 5/1972 | Low et al. | 73/23.35 |
| 3,999,066 | 12/1976 | Osborne | 250/304 |
| 4,244,783 | 1/1981 | Corbett et al. | 176/19 R |
| 4,276,060 | 12/1981 | Aldridge | 55/67 |
| 4,307,620 | 12/1981 | Jiskoot | 73/863.83 |
| 4,435,644 | 3/1984 | Heki | 250/435 |
| 4,469,496 | 9/1984 | Frischmuth et al. | 55/67 |
| 4,504,737 | 3/1985 | Cox et al. | 250/435 |
| 4,591,716 | 5/1986 | Kitaguchi et al. | 250/336.1 |
| 4,618,774 | 10/1986 | Hascal et al. | 250/364 |
| 4,732,581 | 3/1988 | Cheh et al. | 55/67 |
| 4,835,395 | 5/1989 | McManus et al. | 250/435 |
| 4,867,762 | 9/1989 | Pierini et al. | 55/67 |
| 4,935,196 | 6/1990 | Griesbach et al. | 376/314 |

OTHER PUBLICATIONS

Karmen et al. "Measurement of Tritium in the Effluent of a Gas Chromatography Colume" Analytical Chemistry, vol. 35 No. 4 Apr. 1963, pp. 536-542.

*Primary Examiner*—Hezron E. Williams
*Assistant Examiner*—Michael Brock
*Attorney, Agent, or Firm*—Brian R. Tumm; Harold M. Dixon; William R. Moser

[57] ABSTRACT

A system for continuously monitoring the concentration of tritium in an aqueous stream. The system pumps a sample of the stream to magnesium-filled combustion tube which reduces the sample to extract hydrogen gas. The hydrogen gas is then sent to an isotope separation device where it is separated into two groups of isotopes: a first group of isotopes containing concentrations of deuterium and tritium, and a second group of isotopes having substantially no deuterium and tritium. The first group of isotopes containing concentrations of deuterium and tritium is then passed through a tritium detector that produces an output proportional to the concentration of tritium detected. Preferably, the detection system also includes the necessary automation and data collection equipment and instrumentation for continuously monitoring an aqueous stream.

18 Claims, 1 Drawing Sheet

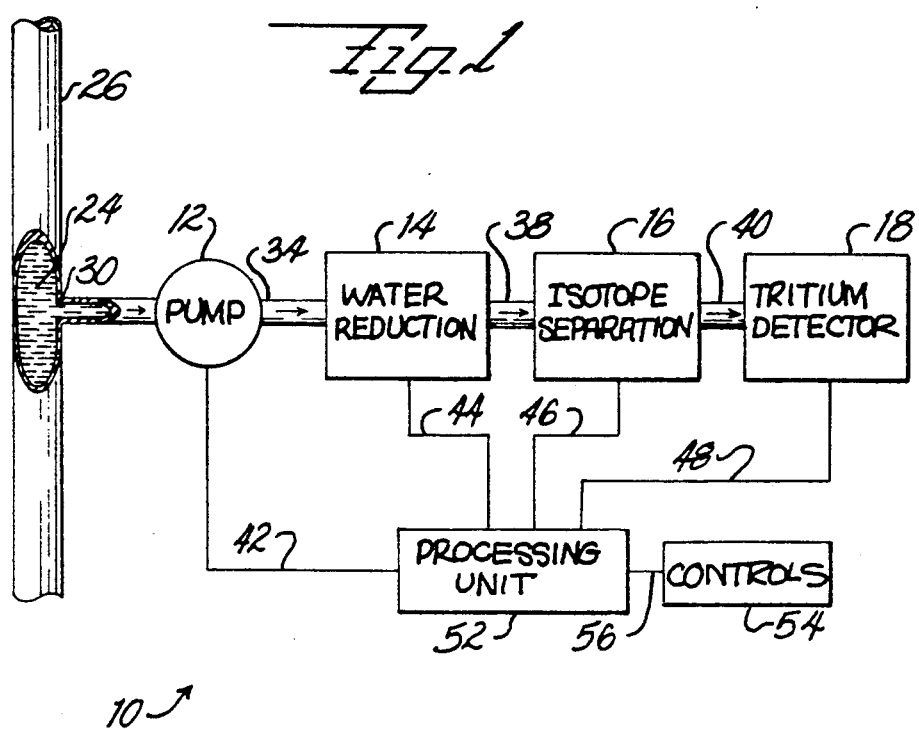

TRITIUM MONITOR

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to devices and methods for monitoring and measuring tritium levels. More particularly, the present invention relates to monitoring the concentration of tritium in aqueous samples.

2. Discussion of Background

Tritium is a radioactive isotope of hydrogen that is produced in nuclear reactors by bombarding lithium with neutrons. Tritium also occurs naturally in small concentrations, and may result from the bombardment of water molecules by a neutron flux or other high-energy radiation. Indiscriminate tritium release to the environment is forbidden by law. Therefore, the presence of tritium in nuclear power generating and production facilities dictates the need for effective tritium monitoring. Furthermore, the sensitivity (or detection limit) of tritium monitors must be appropriate for the particular monitoring application.

Devices and methods for detecting the presence of tritium in liquids and gases are known. Hascal et al, in U.S. Pat. No. 4,618,774, disclose an instrument for measuring tritium and tritium oxide levels in air. The instrument uses a scintillation detector and a pair of scintillators, one serving as a reference. The device compares the measured counting rate of airborne tritium and tritium oxide passing over one scintillator with that of the reference scintillator. The air is condensed onto and evaporated from the surface of the non-reference scintillator.

Osborne et al, U.S. Pat. No. 3,999,066, disclose a system comprising a method and apparatus for continuously monitoring air for the presence of tritiated water vapor. Tritiated water vapor contained in the sample air is transferred to a liquid which is contacted with the air sample. Radioactive noble gases are stripped from the liquid using a gas stream, and the resulting liquid is analyzed for beta radiation of the energy level indicative of the presence of tritium using a detector such as a scintillation counter.

Other methods are also known which monitor tritium levels in liquids and gases. For instance, Corbett et al, U.S. Pat. No. 4,244,783, disclose a method for monitoring tritium levels in the coolant fluid and reactor cover gas of a sodium-cooled nuclear breeder reactor. The tritium is separated by a hydrogen-permeable tube and diffused into a gas discharge device that ionizes the gas. The tritium is monitored by measuring the ionization current produced.

McManus et al, in U.S. Pat. No. 4,835,395, disclose a method and apparatus for continuously monitoring the tritium concentration in liquid aqueous solutions. A series of air streams direct water and tritiated water from the liquid sample to a flow-through ionization chamber. The ion chamber response, along with humidity and temperature measurements, are ultimately used to calculate the tritium content.

SUMMARY OF THE INVENTION

According to its major aspects and broadly stated, the present invention is a device for detecting concentrations of tritium in an aqueous stream. The system can be automated to detect concentrations repeatedly so that changes in the concentration over time can be seen. The system pumps a sample from the aqueous stream to an extracting means which isolates hydrogen, in the form of hydrogen gas, from the balance of the sample. The hydrogen gas is then separated by an isotope separation device into two groups of isotopes: a first group of isotopes containing concentrations of deuterium and tritium, and a second group of isotopes not containing any substantial concentrations of deuterium and tritium. The first group is then analyzed for tritium by a detection system that measures the amount of radiation emitted by the tritium. The amount of radiation measured in the sample indicates the concentration of tritium in the aqueous sample. Preferably, the detection system also includes the necessary automation and data collection equipment and instrumentation for continuously monitoring the tritium concentration data of an aqueous stream.

An important feature of the present invention is the combination of the steps of separating the hydrogen from the sample followed by the division of the hydrogen into two isotopic groups. By making this a two step procedure rather than simply measuring the tritium in hydrogen, the accuracy is greatly increased. Another important feature of the present invention is the use of a magnesium-filled combustion tube to separate the hydrogen by reduction. This technique is well-known and easy step for separating hydrogen but is not known as a step in separating tritium for isotopic monitoring.

Other features and advantages of the present invention will be apparent to those skilled in the art from a careful reading of the Detailed Description of a Preferred Embodiment presented below and accompanied by the drawings.

BRIEF DESCRIPTION OF THE DRAWING

In the drawings,

FIG. 1 is a diagrammatic view of a tritium monitoring system according to a preferred embodiment of the present invention.

DETAILED DESCRIPTION OF A PREFERRED EMBODIMENT

Referring now to FIG. 1, detection system 10 is comprised of a series of components that cooperate to measure the tritium content of a sample. These components include a pump 12 for obtaining an aqueous sample from a stream, a reduction device 14 for extracting the hydrogen from the aqueous sample, an isotope separation device 16 for concentrating the deuterium-tritium fraction of the isotopes in the hydrogen gas from the protium, and a tritium counting device 18.

Reduction device 14 is preferably a magnesium-filled combustion tube. Isotope separation device 16 is preferably a gas chromatograph or a hydrogen absorbing column. Tritium counting device 18 is preferably a counting chamber, an ionization chamber, or mass spectrometer, but it can be any device capable of detecting tritium directly or indirectly and producing an output proportional to the amount of tritium present in the sample.

In a preferred embodiment, an aqueous stream 24 flows through a conduit 26. A tap 30 is made into conduit 26 to allow a sample of aqueous fluid to be diverted by pump 12 and forwarded to system 10. Depending on the pressure of the stream, a control valve may be substituted for pump 12 or used in combination with pump 12 to provide a measured amount of sample to system 10.

When monitoring tritium concentrations, pump 12 periodically or continuously, depending on mode of operation, extracts or pumps samples from conduit 26 through tap 30 to reduction means 14 through a first pipe 34.

Reduction device 14 extracts the hydrogen gas component of the aqueous sample and forwards it to isotope separation device 16 by a second pipe 38. Isotope separation device 16 divides the isotopes of hydrogen in the hydrogen gas into two fractions, a deuterium-tritium portion and a protium portion containing substantially no deuterium or tritium. The first portion is forwarded to detection device 18 through a third pipe 40. Once detection device 18 has ascertained the amount of tritium in the sample, the sample may be vented to the atmosphere.

Devices 12, 14, 16, and 18 are preferably in electrical connection (represented by lines 42, 44, 46, and 48, respectively) with a processing unit 52 that controls the operation and sequencing of each device. Preferably, processing unit 52 is a programmed general purpose or special purpose computer for operating system 10 in either a batchwise or continuous mode for monitoring the concentration of tritium in the aqueous stream over time. Processing unit 52 is operated by a set of controls 54 or user interface, which can be collocated with processing unit 52, or remotely located from unit 52 through an electrical connection (represented by line 56).

In use, pump 12 extracts a sample of aqueous stream 24 from conduit 26 through tap 30. Extraction may occur periodically (in a batch sampling environment) or continuously (in a continuous sampling environment) at a rate appropriate for the proper function of system 10. The aqueous sample is then pumped through first pipe 34 to reduction device 14.

Reduction device 14 extracts and isolates hydrogen in the form of hydrogen gas from the aqueous sample, preferably through the use of a magnesium-filled combustion tube. The isolated hydrogen gas is then sent to isotope separation device 16 via second pipe 38, where the gas is further separated into two isotope groups. The first group of isotopes has concentrations of deuterium and tritium isotopes; the second group of isotopes has substantially no concentrations of either deuterium or tritium isotopes.

The first group of isotopes is then sent through third pipe 40 to tritium detecting device 18. Preferably, the second group of isotopes is removed from detection system 10 and is either discarded or sent to another system for additional sample analysis. Detector device 18, preferably in the form of a counting or ionization chamber, measures the radiation emitted from the tritium concentration of the first isotope group and produces an output signal proportional to the concentration of tritium in the isotope group. Thus, the tritium concentration of aqueous stream 24 can be inferred.

System 10 is capable of analyzing tritium concentrations from ultra-low worldwide background range to greater than 90%. A typical system, for example, could have a sample metering pump 12, a magnesium-filled combustion tube reducing device 14, a small TCAP hydrogen separation device 16 with 1.5 liter columns, and a 1.3 liter counting chamber 18. With this particular system configuration, a 33 ml sample size can be reduced and separated so that the D-T fraction concentration is 100:1. With this degree of concentration and the 1.3 liter counting chamber, a detection limit of 0.2 pCi/ml is possible. By comparison, the same system configuration would provide a detection limit of 30 pCi/ml for a 0.26 ml sample size.

Preferably, the entire sampling and detection process is controlled by processing unit 52. Processing unit 52 collects data from devices 12, 14, 16, and 18 in order to assist in coordinating the operation of the devices. Proper coordination between devices 12, 14, 16, and 18 is essential in detection systems where continuous monitoring of tritium concentration levels is desired.

It will be apparent to those skilled in the art that many changes and substitutions can be made to the preferred embodiment herein described without departing from the spirit and scope of the present invention as defined by the appended claims.

What is claimed is:

1. Apparatus for monitoring the concentration of tritium in an aqueous sample, said apparatus comprising:
   means for extracting hydrogen gas from said aqueous sample, said hydrogen gas having at least two isotopes;
   means for separating said hydrogen gas isotopes into a first group of isotopes and a second group of isotopes, said separating means in fluid communication with said extracting means, said first group having concentrations of deuterium and tritium isotopes, said second group having substantially no deuterium or tritium isotopes; and
   means for detecting said tritium concentration of said first isotope group, said detecting means in fluid communication with said separating means, said tritium concentration of said first isotope group representative of said tritium concentration of said aqueous sample.

2. The apparatus as recited in claim 1, wherein said extracting means further comprises means for reducing said aqueous sample thereby isolating hydrogen from said aqueous sample, and means for capturing said isolated hydrogen in the form of hydrogen gas.

3. The apparatus as recited in claim 1, wherein said extracting means further comprises a magnesium-filled combustion tube.

4. The apparatus as recited in claim 1, wherein said isotope separating means further comprises a gas chromatograph.

5. The apparatus as recited in claim 1, wherein said isotope separating means further comprises a hydride absorption column.

6. The apparatus as recited in claim 1, wherein said detecting means further comprises an ionization chamber, said ionization chamber detecting radiation emitted from said tritium concentration of said first isotope group.

7. The apparatus as recited in claim 1, wherein said detecting means further comprises a mass spectrometer.

8. The apparatus as recited in claim 1, wherein said detecting means produces an output and said apparatus further comprises means in electrical connection with said detecting means and responsive to said output of said detecting means for collecting data, said output proportional to said concentration of said sample, said data collection means having means for recording concentrations of isotopes.

9. The apparatus as recited in claim 1, wherein said apparatus further comprises means for operationally controlling said apparatus, said controlling means in electrical connection with said extracting means, said separating means, and said detecting means.

10. The apparatus as recited in claim 1, wherein said apparatus further comprises means for pumping said sample to said extracting means, said pumping means in fluid communication with said extracting means, said pumping means pumping a measured amount of said sample to said extracting means.

11. Apparatus for monitoring the concentration of tritium in an aqueous sample, said apparatus comprising:
    means for reducing said aqueous sample to isolate hydrogen from said aqueous sample, said hydrogen isolated in the form of hydrogen gas, said hydrogen gas having at least two isotopes;
    means for capturing said hydrogen gas isolated from said reduced aqueous solution;
    means for separating isotopes of said hydrogen gas into a first group of isotopes and a second group of isotopes, said separating means in fluid communication with said capturing means, said first group having a concentration of deuterium isotopes and a concentration of tritium isotopes, said second group having substantially no deuterium or tritium isotopes;
    means for detecting radiation emitted from said tritium concentration of said first isotope group, said detecting means in fluid communication with said separating means and producing an output proportional to said tritium concentration of said aqueous sample; and
    means for collecting data, said collecting means in electrical connection with said detecting means and responsive to said detecting means output, said collecting means having means for recording concentrations of said aqueous sample.

12. The apparatus as recited in claim 11, wherein said reducing means further comprises a magnesium-filled combustion tube.

13. The apparatus as recited in claim 11, wherein said apparatus further comprises means for operationally controlling said apparatus, said controlling means in electrical connection with said extracting means, said separating means, said detecting means, and said collecting means.

14. The apparatus as recited in claim 11, wherein said apparatus further comprises means for pumping said sample to said extracting means, said pumping means in fluid communication with said extracting means, said pumping means carrying a known and measured amount of said sample to said extracting means.

15. The apparatus as recited in claim 11, wherein said detecting means further comprises an ionization chamber.

16. The apparatus as recited in claim 11, wherein said isotope separating means further comprises a hydride absorption column.

17. A method for continuously monitoring the concentration of tritium in an aqueous sample, said method comprising the steps of:
    pumping said aqueous sample to a sample separation means;
    extracting hydrogen gas from said aqueous sample;
    isolating said hydrogen gas from said aqueous sample;
    separating isotopes of said hydrogen gas into a first and second group of isotopes, said first group having concentrations of deuterium and tritium isotopes, said second group of isotopes having substantially no deuterium or tritium isotopes;
    detecting the concentration of tritium from said first group, said detection using an ionization chamber and producing an output proportional to said concentration of said sample; and
    collecting said output produced from said tritium detection.

18. The method as recited in claim 17, wherein said isotope separating step further comprises the step of absorbing said isotopes in a hydride absorption column.

* * * * *